United States Patent

Harttig

(10) Patent No.: US 8,062,232 B2
(45) Date of Patent: Nov. 22, 2011

(54) TEST ELEMENT WITH ELASTICALLY MOUNTED LANCET

(75) Inventor: Herbert Harttig, Neustadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 588 days.

(21) Appl. No.: 11/673,082

(22) Filed: Feb. 9, 2007

(65) Prior Publication Data

US 2007/0182051 A1   Aug. 9, 2007

(30) Foreign Application Priority Data

Feb. 9, 2006   (EP) .................................. 06101434

(51) Int. Cl.
*A61B 5/00* (2006.01)

(52) U.S. Cl. ....................................... 600/583; 606/181

(58) Field of Classification Search ................ 600/583; 606/181–183
See application file for complete search history.

(56) References Cited

U.S. PATENT DOCUMENTS

| | | | |
|---|---|---|---|
| 5,733,300 A * | 3/1998 | Pambianchi et al. | 606/181 |
| 6,561,989 B2 * | 5/2003 | Whitson | 600/573 |
| 7,282,058 B2 * | 10/2007 | Levin et al. | 606/181 |
| 2002/0052618 A1 * | 5/2002 | Haar et al. | 606/181 |
| 2003/0050573 A1 | 3/2003 | Kuhr et al. | |
| 2003/0211619 A1 * | 11/2003 | Olson et al. | 436/44 |
| 2004/0092997 A1 * | 5/2004 | Levin et al. | 606/181 |
| 2004/0127818 A1 * | 7/2004 | Roe et al. | 600/583 |
| 2004/0133227 A1 * | 7/2004 | Shang et al. | 606/182 |
| 2004/0163987 A1 * | 8/2004 | Allen | 206/438 |
| 2004/0260325 A1 | 12/2004 | Kuhr et al. | |
| 2005/0004494 A1 * | 1/2005 | Perez et al. | 600/583 |
| 2006/0020228 A1 * | 1/2006 | Fowler et al. | 600/583 |
| 2006/0085020 A1 * | 4/2006 | Freeman et al. | 606/181 |

FOREIGN PATENT DOCUMENTS

| | | |
|---|---|---|
| EP | 1174083 A2 | 1/2002 |
| EP | 1459683 A1 | 9/2004 |
| EP | 1611849 A1 | 1/2006 |
| EP | 1360932 B1 | 1/2007 |
| WO | 9835225 A1 | 8/1998 |
| WO | 2004066822 A2 | 2/2007 |

* cited by examiner

*Primary Examiner* — Max Hindenburg
*Assistant Examiner* — Michael C Stout
(74) *Attorney, Agent, or Firm* — Kristina E. Swanson; Roche Diagnostics Operations, Inc.

(57) ABSTRACT

This invention generally relates to a method for producing an analytical system, and to a analytical system for detecting an analyte in a body fluid. The analytical system comprises a test element and a lancet which is movable relative to the test element and which is received on the test element. The lancet is connected to the test element via an elastomer spring.

19 Claims, 4 Drawing Sheets

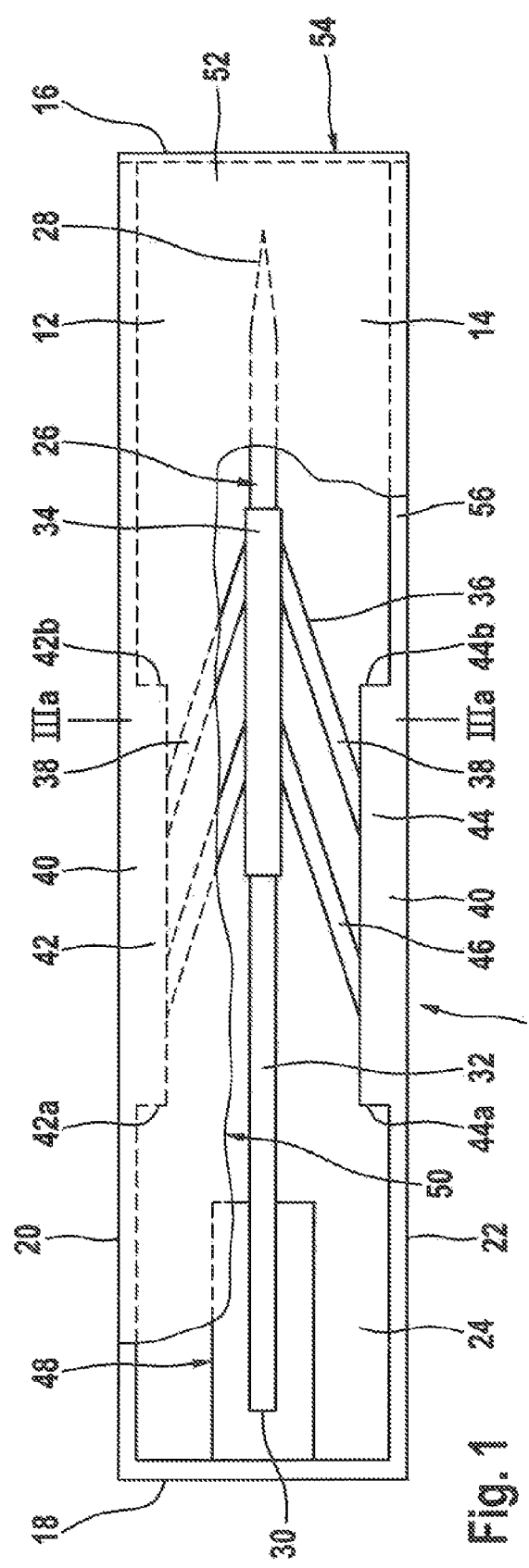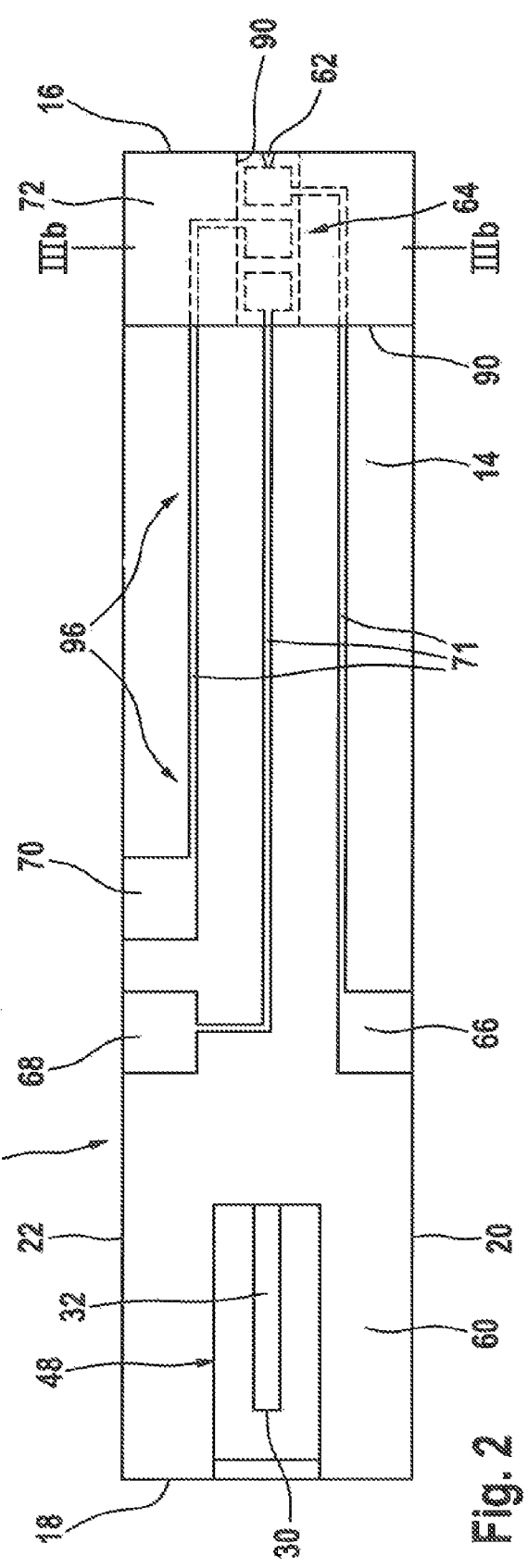

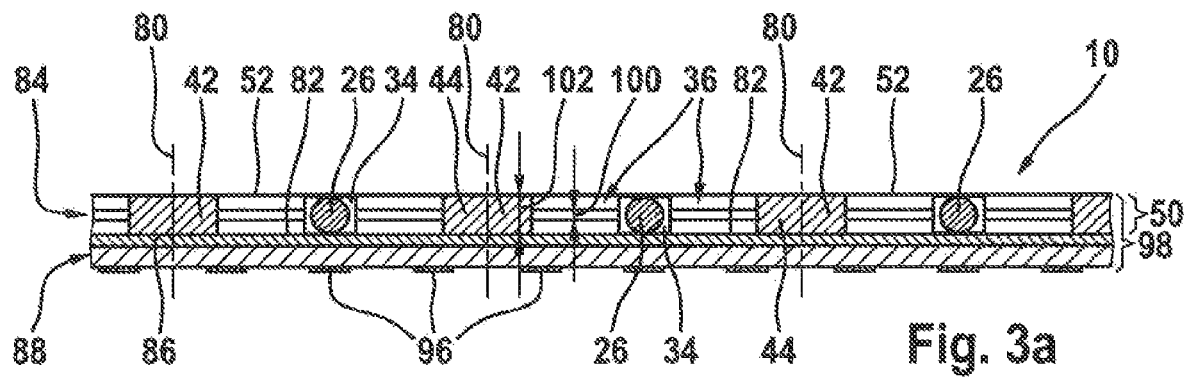
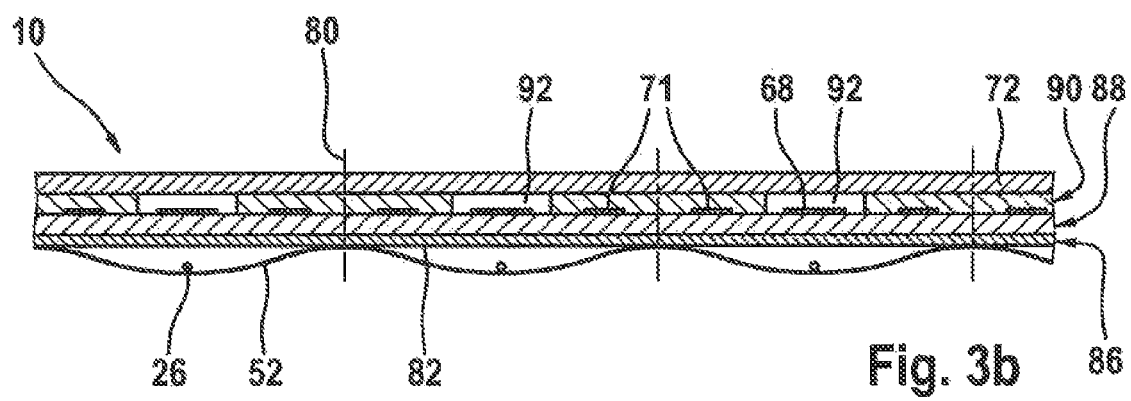
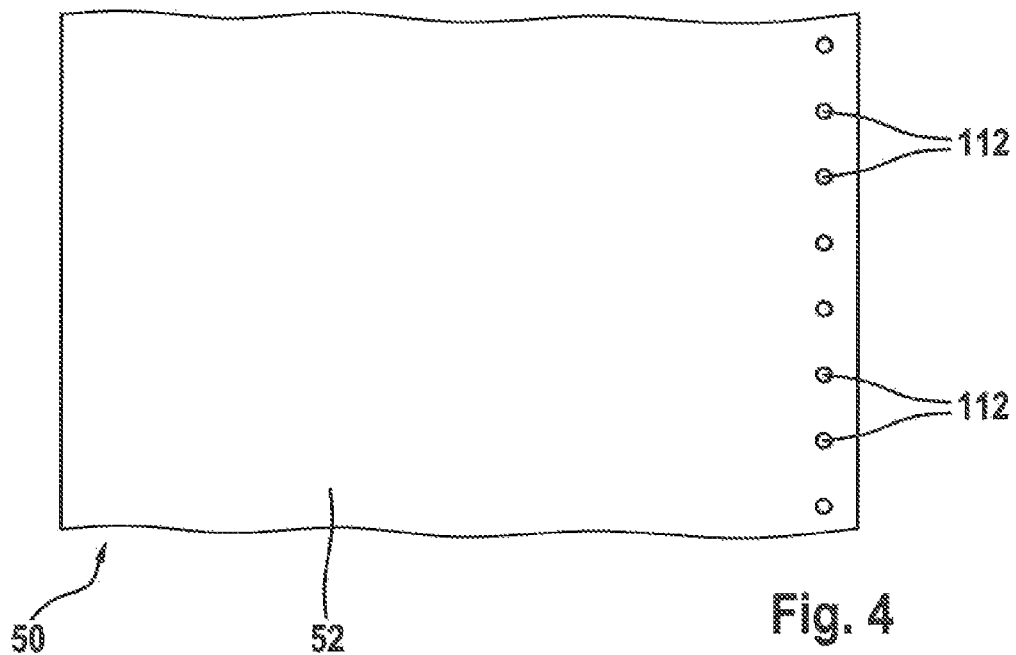

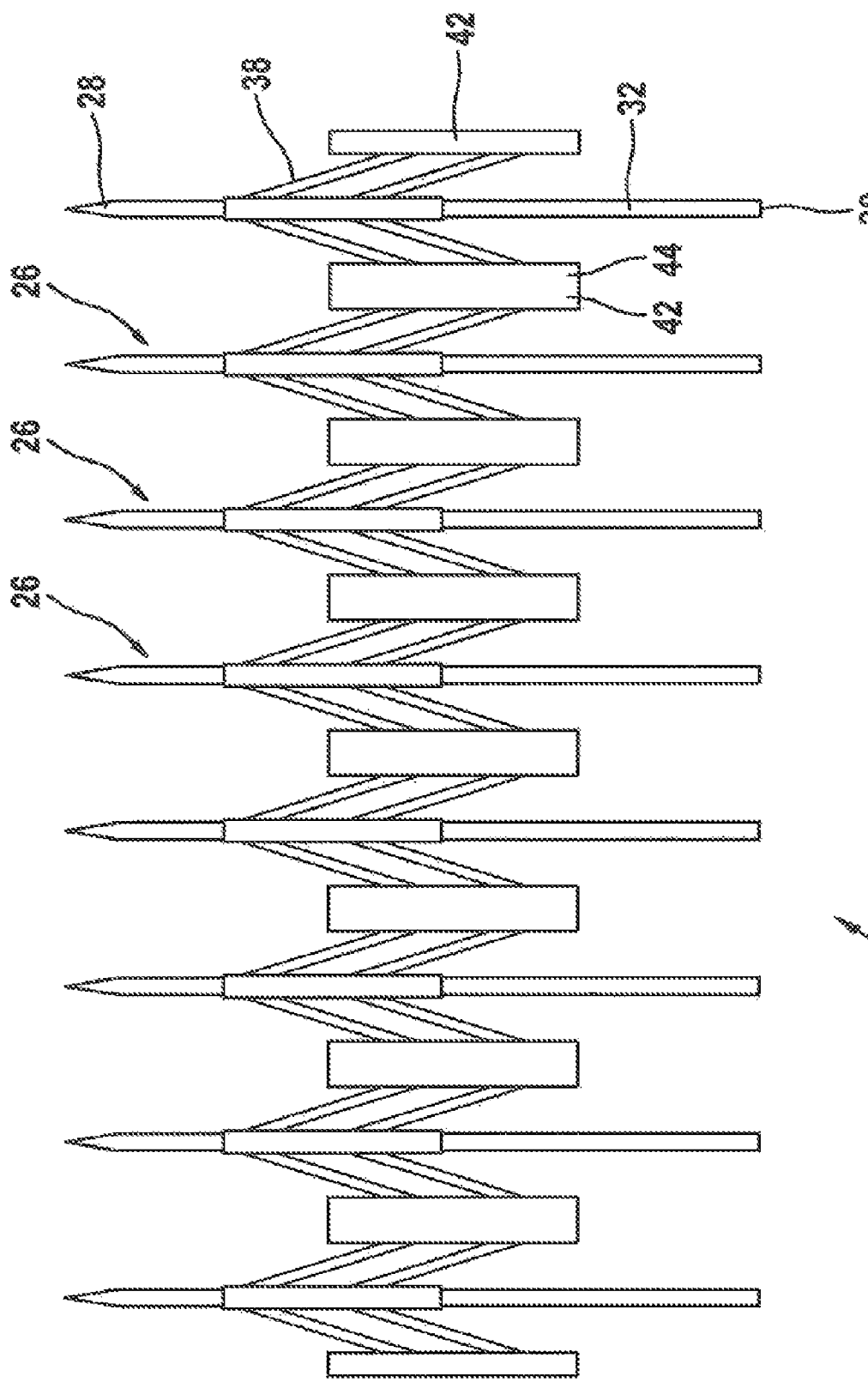

TEST ELEMENT WITH ELASTICALLY MOUNTED LANCET

REFERENCE TO RELATED APPLICATIONS

The present application is based on and claims priority to European Patent Application No. 06101434.6, filed Feb. 9, 2006, which is hereby incorporated by reference in its entirety.

TECHNICAL FIELD

The invention generally relates to an analytical system, in particular a test strip for detection of analytes in body fluid, with a lancet for perforating the skin of the test subject.

BACKGROUND

Test elements in the form of test strips for detection of analytes in blood have been state of the art for some time now. Test elements in test strip form are used particularly in the field of blood sugar measurement. Measurement of blood sugar levels by the patients themselves has led to continued development of test systems and of the test strips, mainly designed as test strips, used in said systems. The aims of this development were improved analysis, improved operating safety, a reduction in the volumes of blood that have to be taken from the patient, and simplified handling, particularly a reduction in the handling steps needed.

To obtain the blood for carrying out the analysis by means of test elements designed as test strips, various designs of puncturing aids have been developed which are used to perforate the patient's skin and to allow emergence of the quantity of blood needed for the analysis. To improve handling, test elements have been proposed that permit a combination of puncturing and measuring devices.

Prior art systems have disclosed a puncturing aid with a lancet system that is protected against reuse.

The puncturing aid is used to create an opening in the skin and typically comprises a housing into which a lancet system can be inserted. The housing moreover comprises a retaining element which cooperates with a corresponding retaining element of the lancet system, so that the lancet system can be positioned in the housing at a defined location. The housing moreover comprises an opening from which a needle tip of at least one needle of the lancet system can emerge during a puncturing procedure. A drive mechanism for driving the at least one needle is provided, so that the needle can be transferred from a rest position to a puncturing position. The needle is connected to a needle body in such a way that the needle and a protection area of the needle body are movable relative to one another. In a first position, the protection area of the needle body at least partially surrounds the needle tip, whereas, in a second position, the needle and the protection area of the needle body are arranged relative to one another such that the needle tip is freed from the protection area of the needle body. The needle body moreover includes a blocking mechanism which is actuated through cooperation with the puncturing aid and changes the needle body so that, after the lancet system has been ejected from the puncturing aid, interaction between the retaining element of the puncturing aid and retaining element of the lancet system is prevented upon renewed insertion.

According to know solution, the metal needle is secured on a plastic body and is fixedly connected to the plastic body. An area is formed on the plastic body for the purpose of coupling the lancet system to a drive ram, so that the needle can be moved along the axis in the direction of puncturing. The rear area of the plastic body is designed for coupling to the drive ram such that two arms, provided with projections, permit a form-fit connection of the plastic body to the puncturing aid. Therefore, producing a coupling between the lancet needle and the puncturing drive mechanism represents an additional outlay, both in terms of the lancet needle and in terms of the measurement appliance.

The solutions known from the prior art, regarding a system composed of a combination of test element and puncturing aid, are all either associated with the disadvantage of having a large overall size or require a coupling to the measurement appliance, which, from the technical point of view, is an unsatisfactory situation. Therefore, there is a need to have a system is comprised of test element and puncturing aid that overcomes the disadvantages of prior art.

SUMMARY

One of the objects of the invention is to make available a test element/puncturing aid system that has a simple structure and can be received in the measurement appliance without a coupling.

According to one aspect of the invention on a substantially flat test element, a lancet or a needle is arranged and is connected movably to the test element via an elastic material. The test element comprises a capillary through which a blood sample, accessed after the skin has been punctured, is transported from the patient's skin to a measurement area contained in the test element. The opening of the capillary is located on the front edge of the test element in order to take up the blood sample from the patient's skin.

One or more measurement areas for detection of the analyte, and electrical contacts or optical windows for recording the detection reaction, are formed on one flat face of the test element. The measurement areas are applied to the test element, for example, in the form of a film coating of the corresponding face of the test element. On the other flat face of the test element, a puncturing aid in the form of a lancet or needle is attached. Instead of a needle with a round or circular cross section, it is also possible to use a puncturing aid that has a square or rectangular cross section. The lancet is oriented parallel to the longitudinal axis of the test element and is located approximately centrally in relation to the width of the test element. The end of the lancet directed towards the capillary is ground to a point, or is formed into a sharp tip in some other way, for example by laser cutting or an etching process. A wide variety of profiles can be used that are suitable for creating an opening in the skin. The rear end of the lancet, remote from the lancet tip, is blunt and has an end face.

In yet another aspect of the invention, the lancet integrated test system comprising a test element and a lancet. The lancet is movable relative to the test element and is connected to the test element by a connection composed of at least one cord of an elastic material. On the one hand, the cord is secured centrally on the lancet, and, on the other hand, it is secured on the two longitudinal sides of the test element. In addition to a cord-like connection of the lancet to the longitudinal sides of the test element, the connection between the lancet and the test element can also be configured as threads or as a number of strips situated between the longitudinal sides of the test element and the lancet, which is arranged centrally on a flat face of the test element.

In yet another aspect of the invention, in the rest position, the sharp end of the lancet is located inside the contour of the test element. The rear, blunt end of the lancet can also lie inside the contour of the test element or can also extend beyond the contour of the test element. The length of the lancet is dimensioned such that it is shorter than the length of the test element. At the rear edge of the test element remote from the capillary opening, the test element is provided with a V-shaped or rectangular recess through which the puncturing drive mechanism of the measurement appliance contacts the rear end of the lancet and causes an advance movement of the lancet relative to the test element.

The lancet is enclosed by a film pouch, at least in the area of the sharp tip. After sterilization, with β or γ rays, the film pouch ensures permanent sterility of the lancet tip during storage. The film pouch is fixedly connected to the outer edge of the test element, for example welded to it. Together with the film pouch, the elastic material is also connected to the test element. The connection of the film pouch to the test element is made following the sterilization. This ensures that the detection chemicals for detecting the analyte or analytes are not subjected to sterilization and their efficacy is not compromised.

In yet another aspect of the invention, a test element can be handled manually, without any danger of accidentally touching the unused or used tip of the lancet and without any danger of inadvertent injury. The elastic connection between the test element and the lancet ensures that the tip of the lancet is drawn back into the contour of the test element after the puncture has been made, thereby ruling out any possibility of inadvertent injury. The connection in the form of an elastomer spring, made of a rubber elastic material, between the longitudinal sides of the test element and the lancet body represents a very simple mechanism for moving the lancet during use in a measurement appliance. If the lancet system proposed according to the invention is fitted in a measurement appliance, the latter can be produced without a coupling site, since the blunt end of the lancet simply has to be acted upon by the advance movement of a ram, for example of the puncturing drive mechanism arranged in the measurement appliance, as a result of which the lancet is pushed out from the contour of the test element, past the front edge of the latter, in order to carry out a puncturing movement counter to the action of the elastomer spring. On the measurement appliance, there is no need for a coupling to the lancet that is received movably on the test element. The elastomer spring functions more reliably and is less susceptible to failure than many mechanical couplings between the measurement appliance and the lancet. The work involved in forming a coupling on the lancet can also be avoided.

In yet another aspect the lancet when penetrating the film pouch during the puncturing movement, the lancet received movably by the test element and enclosed by a film pouch loses less energy. Thus, a higher speed of puncturing is ensured, which reduces the patient's subjective experience of pain.

Formed on the face of the test element directed away from the lancet is the aforementioned measurement area, to which a blood sample is transported from the skin of the patient by capillary forces after the puncture has been made. The analyte can be detected by optical means or by electrochemical means in the measurement area. The lancet system proposed is used for detection of clinical and chemical parameters or of coagulation parameters, for example glucose, lactate, electrolytes (e.g. $Na^+$, $K^+$, $Ca^{++}$), cholesterol or prothrombin, among other parameters.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The followings detailed description of the embodiments of the present invention can be best understood when read in conjunction with the following drawings, where like structure is indicated with like reference numerals and in which:

FIG. 1 shows a front face of the analytical system proposed according to the invention, comprising a lancet received elastically on a test element, FIG. 2 shows the rear face of the system according to the view in FIG. 1, FIG. 3a shows a cross section through the layered structure of the system according to the cross-sectional profile IIIa-IIIa in FIG. 1 at about half way along its length, FIG. 3b shows a cross section through the layered structure of the system according to the cross-sectional profile IIIb-IIIb in FIG. 2, near the front end, FIG. 4 shows a view of the sterile protective band of film, with the pilot holes permitting orientation, FIG. 7 shows a continuous band of lancets.

Figure 5:
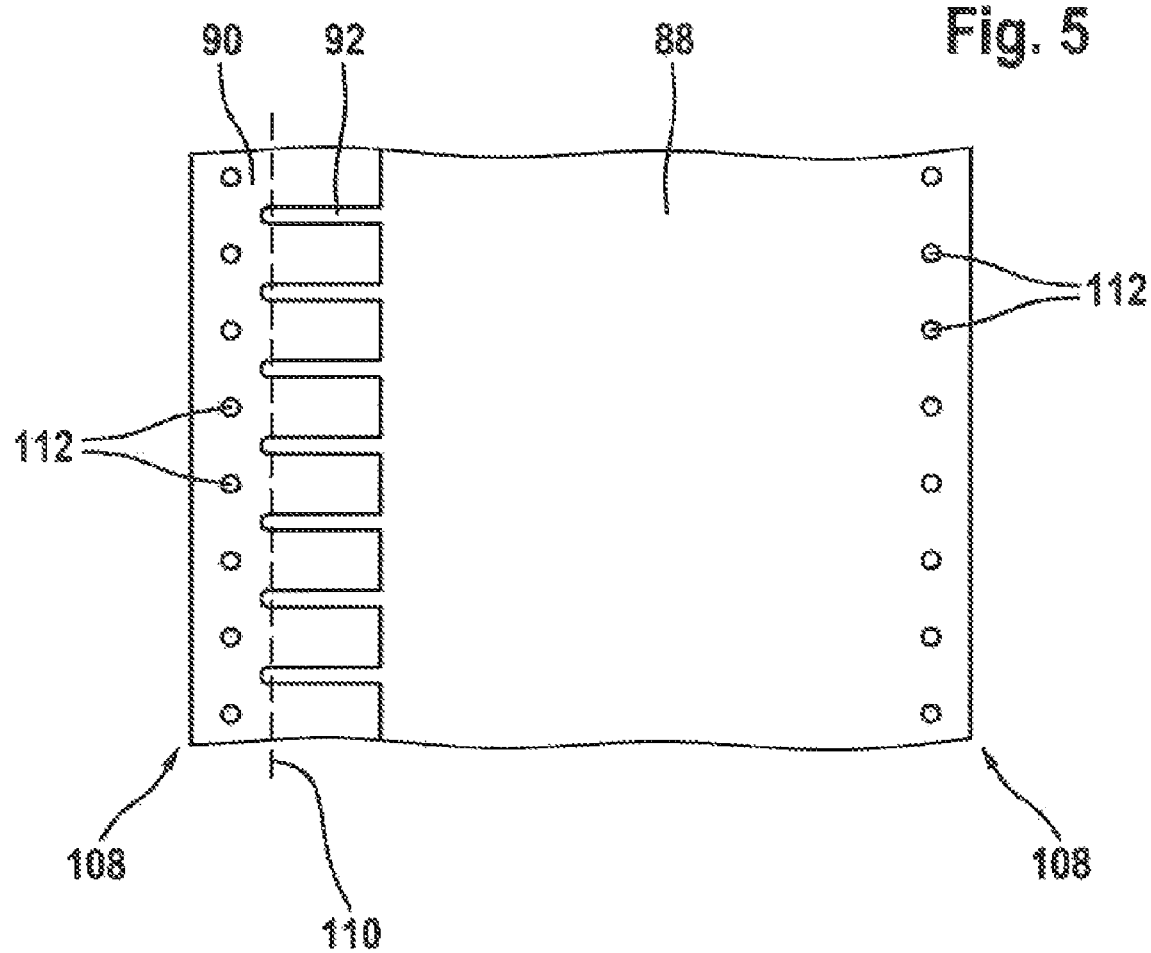
FIG. 5 shows the support band with pilot holes on both sides.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment (s) of the present invention.

In order that the invention may be more readily understood, reference is made to the following examples, which are intended to illustrate the invention, but not limit the scope thereof.

DETAILED DESCRIPTION

The following description of the preferred embodiment is merely exemplary in nature and is in no way intended to limit the invention or its application or uses.

The term lancet system or the analytical system, as used below, is to be understood as a combination of a test element 14 with a puncturing aid which is mounted movably thereon and which is designed as a lancet. The test element 14 can be a test strip which is substantially flat and is configured in such a way that it can be inserted into a measurement appliance for determining an analyte in a human or animal body fluid. The lancet 26 can be a needle of circular cross section or a material having a square or rectangular cross section which is provided with a sharp tip or a sharp cutting edge in order to create an opening in the skin of the patient.

Measurement appliance is to be understood hereinafter as meaning one that receives the lancet system and displays the analysis results of the body fluid analysis carried out in a measurement area of the lancet system.

Measurement area is to be understood below as meaning the area of the lancet system within which the collected human body fluid is determined by reagents, to give one example, applied to the test element of the lancet system. Within the measurement area, the measurement can take place by electrochemical means and also optically.

Film pouch is understood below as a plastic film, sealed on all four edges, and in which there is no connection between the two plies of plastic film, or in which the twin ply is formed by folding at one edge. To form the film pouch, the two plies of the plastic film are connected fixedly to one another, at the remaining three edges.

Rest position is understood below as that position of the lancet or needle on the test element in which the needle or lancet remains without the effect of external forces. The elastic material is relaxed in the rest position.

Cuttings are understood as recesses in the area of the elastomer spring which are formed by shaping during formation of the elastic band in the liquid or partially liquid state of the elastomer material.

FIG. 1 shows the front face of the lancet system proposed according to the invention, comprising a test element with a lancet mounted elastically thereon.

It will be seen from the view of the front face 12 of a lancet system 10 that a test element 14 has a surface 24 which is delimited by a front edge 16, a rear edge 18, a first longitudinal side 20 and a second longitudinal side 22. Along the first longitudinal side 20, the rear edge 18 and the second longitudinal side 22, a peripheral edge 56 extends about the surface 24 of the test element 14. The peripheral edge 56 comprises a first widened area 42 on the first longitudinal side 20 and the second longitudinal side 22 of the test element 14, and a second widened area 44 on the second longitudinal side 22. These widened areas 42 and 44 each represent a spring abutment 40 for an elastomer spring 36.

A lancet 26 is arranged centrally on the surface 24 of the test element 14. In the embodiment shown in FIG. 1, the lancet 26 is designed as a needle and accordingly has a circular cross section. Instead of a needle-shaped lancet 26, it is of course also possible to design the lancet 26 with other than needle-like geometries (see the alternative embodiments shown in FIGS. 6 and 6a.

The lancet 26 comprises a lancet tip 28, which is sharpened to a point. The lancet tip 28 can be provided with a ground surface, which can be provided in a wide variety of geometries so that, upon insertion of the lancet tip 28 into the skin of the test subject, a skin opening is created that allows a body fluid to emerge. The lancet 26 moreover comprises a lancet body 32. At the end remote from the lancet tip 28, the lancet body 32 has a blunt end 30. The blunt end 30 can be designed, for example, simply as a flat surface. The lancet body 32 of the lancet 26 is enclosed at about the middle by a plastic sheath 34.

An elastomer spring 36 extends between the plastic sheath 34 of the lancet body 32 and the spring abutments 40 formed at the first widened area 42 and at the second widened area 44. The elastomer spring 36 has at least one elastomer cord 38 on both sides of the lancet 26. The areas of the elastomer spring 36 extending between the plastic sheath 34 of the lancet body 32 and the spring abutments 40 can be cord-like, thread-like or strip-shaped. The elastomer spring 36 is formed by punches, incisions or cuttings 46 being made in a hot-melt elastomer (e.g. Geniomer produced by Wacker, Burghausen, or Pellethane produced by Dow Plastics). The individual cords 38 are formed by the punches, incisions or cuttings 46 in an area of the hot-melt elastomer in which the latter has a reduced thickness of, for example, at most 200 µm. It will be seen from the view in FIG. 1 that the elastomer spring 36 shown there has two individual cords 38 on both sides of the plastic sheath 34 of the lancet body 32, which individual cords 38 elastically connect the plastic sheath 34 of the lancet body 26 to the first widened area 42 and to the second widened area 44 of the peripheral edge 56.

In the area of the rear edge 18 of the lancet system 10, a recess contour 48 is formed in which upon insertion of the lancet system 10 into a measurement appliance the peripheral edge 56 at the rear edge 18 and the surface 24 of the test element 14 can be optionally incised in order to expose the blunt end 30 of the lancet 26. Although the recess contour 48 in the view according to FIG. 1 is rectangular it may also be semicircular or V-shaped. However, the incising of the lancet system 10 along the recess contour 48 in the area of the rear edge 18 of the lancet system 10 is not absolutely necessary. The separation of the material of the lancet system 10 along the recess contour 48 can take place during insertion of the lancet system 10 into a measurement appliance, can be done manually, or can be completely omitted.

The lancet system 10 shown from the front in FIG. 1 comprises a sterile protective band of film which forms a film pouch 50 and encloses the lancet 26 and the elastomer spring 36. The undersides 82 of the film pouch 50 is fixedly connected, for example welded, to the test element 14, along the peripheral edge 56 thereof. The film pouch 50 is folded along the front edge 16 of the lancet system 10; a fold lying in front of the lancet tip 28 is designated by reference number 54. The top face 62 of the film pouch 50 is fixedly connected, along the peripheral edge 56 to the underside 82. In the region of the widened areas 42 and 44, the top face 52 of the film pouch 50 is fixedly connected to the top face of the widened areas 42 and 44, and the underside 82 of the film pouch 50 is fixedly connected to the underside of the widened areas 42, 44. Narrow edges 42a, 42b, 44a and 44b of the widened areas 42, 44 are flattened and merge in a gas-tight and germ-proof manner into the connection between the top face 52 and underside 82 of the film pouch 50.

The view according to FIG. 2 is a plan view of the rear face of the lancet system according to the invention shown from the front in FIG. 1.

It will be seen from the view in FIG. 2 that a film with an electrode structure 96 is applied to a rear face 60 of the lancet system 10. The film with electrode structure 96 is preferably a film which is made of an electrically conductive material, for example gold, and in which conductor tracks 71 extend between a measurement area 64 on the rear face 60 of the test element 14 and connect the measurement area 64 to a first electrode 66 on the first longitudinal side 20 and to two further electrodes 68 and 70 on the second longitudinal side 22 of the test element 14.

On the front edge 16 of the test element 14 there is a capillary inlet 62 of a capillary 92 through which, for example, a body fluid such as blood, emerging from an opening created by the lancet tip 28 in the skin of a test subject, passes into the measurement area 64. In the measurement area 64, an analyte in the body fluid from the test subject can be detected, for example by electrochemical means. In addition to an electro-chemical detection method, an optical detection method for determining an analyte in a body fluid from a test subject can also be effected in the measurement area 64. In this case, instead of the film with electrode structure 96, optical displays can be formed inside the measurement area 64, for example optical windows, and the electrode structure 96 could then be dispensed with. The measurement area 64 on the rear face 60 of the test element 14 is closed off by a cover film 72. A spacer layer 90 bridges the conductor tracks 71 to the electrodes 66, 68 and 70.

At the rear edge 18 of the rear face 60 of the test element 14 according to the view in FIG. 2, the material of the surface 24 of the test element 14 is removed along the recess contour 48 shown in FIG. 1. In this way, the rear area of the lancet body 32 and parts of the peripheral edge 56 are visible in FIG. 2. If the material of the test element 14 is removed in the area of the recess contour 48, as is shown in FIG. 2, the energy of a puncturing drive mechanisms for permitting a rapid puncture movement can be applied unimpeded to the lancet body 32 of the lancet 26 at the blunt end 30.

The lancet system 10 proposed according to the invention operates in the following way:

The lancet system 10 is fitted manually or automatically into the measurement position in a measurement appliance. When inserting the lancet system 10, the film pouch surrounding the rear end of the lancet system 10 can be incised on both sides of the lancet 26 in the area of the recess contour 48. The incision can also be made later in the measurement appliance, by the puncturing drive mechanism present therein, or can be omitted entirely. The front edge 16 of the lancet system 10 preferably assumes such a position that a user can bring the front edge 16 into contact with the skin, for example of a finger. The puncturing drive mechanism presents in the measurement appliance is then tensioned. The lancet system 10 is brought into contact with the skin via its front edge 16A, and a trigger for the puncturing drive mechanism in the measurement appliance is activated. The puncturing drive mechanism can also be triggered by sufficiently powerful pressure being applied, for example by the finger, on the front edge 16 of the lancet system 10. Upon activation of the trigger, the puncturing drive mechanism of the measurement appliance is set in motion. An advancing element of the puncturing drive mechanism, designed for example as a ram, pushes the lancet 26 forwards in the direction of the front edge 16 of the lancet system 10. On its way forwards, the lancet tip 28 of the lancet 26 first pierces the film pouch 50 surrounding the lancet 26 at the fold 54 and then penetrates into the skin of the test subject. The depth of penetration of the lancet tip 28 of the lancet 26 into the skin is determined by the advance of a ram element, for example, of the puncturing drive mechanism. The puncture depth can be set on the measurement appliances by adjusting the advance travel of the ram, for example.

With the forward movement of the lancet 26 relative to the test element 14, the at least one elastic cord 38 of the elastomer spring 36 elastically fixing the lancet 26 on the test element 14 is also pretensioned. When the end of the advance movement of the puncturing drive mechanism is reached, the latter travels back to its starting position. By contrast, the at least one tensioned elastic cord 38 of the elastomer spring 36 draws the lancet 26 back into the film pouch 50 that has already been pierced during the puncture movement.

A drop of blood or body fluid emerges through the puncture made in the skin. The opening of the capillary 62 is brought into contact with the drop of blood either automatically or manually. The emerging blood or body fluid is taken up by suction through the capillary 92 and wets the measurement area 64 on the rear face 60 of the test element 14 of the lancet system 10. The measurement of the analyte concentration within the measurement area 64 takes place in a manner known per se. After completion of the measurement, the used lancet system 10 is discarded or is transferred into a magazine for collection of used lancet systems 10.

The views according to FIGS. 3a and 3b are cross sections through the lancet system proposed according to the invention, which is shown from the front in FIG. 1 and from the rear in FIG. 2.

The cross-sectional view according to FIG. 3a shows that the lancet system 10 has a layered structure 98.

From the layered structure 98 shown in FIG. 3a, it will be seen that the lancet system 10 can be produced as a continuous band which, on a top face, comprises a continuous band 84 with lancets 26 that are spaced apart from one another and are each enclosed by the plastic sheath 34. A large number of lancets 26, spaced apart from one another by the width of a test element, are connected via a hot-melt elastomer (for example Geniomer produced by Wacker, Burghausen) to form a continuous band 84. This continuous band 84 comprising mutually spaced-apart lancets 26 is enclosed at both ends by the film pouch 50. In FIG. 3, the top face of the film pouch 50 is indicated by reference number 52, and the underside of the film pouch 50 is indicated by reference number 82. By means of the film pouch 50, the continuous band 84 with the individual lancets 26 connected to one another by the elastic elastomer is sealed off by the film pouch 50. It will be seen, from the view according to FIG. 3a, that the plastic sheath 34 enclosing the individual lancets 26 is connected via the individual cords 38 of the elastomer spring 36 to the first widened area 42 and to the second widened area 44. The first widened area 42 or second widened area 44 of the lancet system 10 has a thickness indicated by reference number 102 and corresponding to about ¼ to ¾ of the thickness of the lancet 26. The elastomer spring 36 is formed in the hot-melt elastomer at a thickness 100, which is a maximum of 200 μm. The plastic sheath 34 extends along the length of the lancet 26 by at least ¹⁄₁₀ of its length. The widened first and second areas 42, 44 of the continuous band 84 extend in a width of between ¹⁄₁₀ and ¼ of the width of the test elements 14 and have a length which is at least ¹⁄₁₀ of the length of the lancet 26. The elastomer spring 36 indicated in FIG. 3a (cf. view in FIG. 1) is produced by punching or cutting or shaping within the areas of the continuous band 84 formed in the thickness 100. The continuous band 84 is bonded by means of an adhesive layer 86, for example a hot-melt adhesive, to a band of film 88 that serves as a support band. In the view according to FIG. 3b, along section IIIb-IIIb from FIG. 2, a two-sided adhesive spacer layer 90 extends above the band of film 88 and has capillary channels 92 formed in it via which the body fluid collected at the puncture site is transported to the measurement area 64 (not shown in FIG. 3b) of the lancet system 10. The film with electrode structure 96, shown on the rear face 60 of the lancet system 10 in FIG. 2, is located on the underside of the band of film 88. The capillary channels 92 and the spacer layer 90 are covered by the cover film 72 which is shown partially in FIG. 2 and there covers the measurement area 64 of the lancet system 10. Reference number 52 designates the top face of the film pouch 50 made of a sterile protective band of film.

In the view according to FIG. 3a, the lancets 26 connected to one another within the continuous band 84 are designed as needles. The lancets 26 can be made from a special-grade steel with a diameter of 0.8 to 0.25 mm. The lancet tip 28 is ground to a point, and a wide variety of ground surfaces are possible that permit perforation of the skin of a test subject. To produce the test strips according to the invention, a large number of lancets 26, at a mutual spacing of one test element width, are connected by a hot-melt elastomer (Pellethane produced by Dow Plastics) to form a continuous band 84. It is ensured that the individual lancets 260 are enclosed by the elastomer along at least ¹⁄₁₀ of their length, as a result of which the plastic sheath 34 is formed. A widened area is formed centrally between two lancets 26, see the first widened area 42 and second widened area 44 whose widths are at least ¹⁄₁₀ and at most ¼ of the width of the test element 14 and which extend along at least ¹⁄₁₀ of the length of the lancet 26. The widened areas 42 and 44 have a thickness 102 which measures ¼ to ¾ of the thickness of the lancet 26. Between the lancet 26 and the first and second widened areas 42 and 44, the continuous band 84 is reduced in thickness to a thickness of at most 200

µm (reference number 100). In this area of reduced thickness 100, at least two individual cords 38 (compare plan view according to FIG. 1) of the elastomer spring 36 are formed by punching, cutting or incision, which individual cords 38 on both sides of the lancet 26 create connections to the first and second widened areas 42 and 44 acting as spring abutments 40.

While controlling the spacing of the lancets 26 from one another and the position of the lancets 26, the continuous band 84 (cf. view according to FIG. 7) is transported onto the sterile protective band of film from which the film pouch 50 is formed. The sterile protective band of film is characterized by a low to moderate tear strength, by good thermal weldability and by its ability to be sterilized by radiation. The sterile protective band of film can, for example, be made from a foamed OPP (DuPont Teijin Films). The width of the sterile protective band of film is more than twice the length of the individual lancets 26. The sterile protective band of film is provided on one side with pilot holes 112, shown in FIG. 4. The plot holes 112, which are formed in FIG. 4 on the sterile protective band of film, and shown in FIG. 4 from the direction of the top face 52, permit an orientation and exact alignment of the individual layers 84, 88, 90 of the layered structure 98 relative to one another, as shown in FIG. 3a. Since these are made of plastic material, it is entirely possible that they may become offset relative to one another during the production of the lancet system 10, so that an exact orientation of the individual layers of the layered structure 98 of the lancet system 10 is achieved using the pilot holes 112 according to FIG. 4. The continuous band 84 with the individual, interconnected lancets 26 is thermally connected to the sterile protective band of film at the first and second widened areas 42 and 44. The sterile protective band of film is folded over the lancet tips 284 to form a film pouch 50. The turned-back fold 54 lies in front of the lancet tips 28. The resulting film pouch 50 is thermally sealed, so that the individual lancets 26 on each lancet system 10 are individually packed and sterilized. The resulting band 84 is wound up and undergoes sterilization, for example by radiation.

In parallel with the production of the continuous band 84 with the lancets 26 that are individually enclosed by the film pouch 50, the test elements 14 are produced on a support band 88. This band is a Melinex film with a thickness of 350 µm (manufacturer: Huhtamaki Deutschland, Ronsberg/Allgäu) in which the pilot holes 112 shown in FIG. 5 are arranged at a defined distance from one another that corresponds to an integral multiple of the width of one test element 14.

The underside of the support band 88 is coated with a film having electrode structures 96, from which, after removal of excess material, the individual electrodes 66, 68, 70 and conductor tracks 70 extending into the measurement area 64 are formed. Enzyme electrodes can be formed by applying an electrochemical detection reagent, for example a reagent paste. The spacer layer indicated by reference number 90 in FIG. 3a comprises the capillary channels 92 and is closed off by a hydropohilic cover film 72, so that sample fluid can be transported through the capillary channels 92, which are closed off by the cover film 72 and laterally delimited by the space layer 90, to the electrode connections of the electrodes 66, 68 and 70 lying in the measurement area.

At a distance from the capillary 62 shorter than the length of the lancet 26, and in alignment with the capillary 62, rectangular recesses are formed in the support band 88, these recesses being shown by recess contour 48 in connection with the description of FIGS. 1 and 2. The width of the recess contour 48 corresponds at least to the width of the ram provided on the appliance. The length of the recess contour 48 viewed in the direction of puncturing, results from the dimensions of the parts involved and from the desired travel of the lancet tip 28.

While the recess contour 48 in the views according to FIGS. 1 and 2 is rectangular, it is alternatively possible for the recess contour 48 to have a semi-circular or V-shaped form, for example. This ensures that an advancing element of a puncturing drive mechanism can act unimpeded on the blunt end 30 of the lancet body 32, so that the puncturing movement of the lancet 26 for creating a perforation in the skin of the test subject can be effected at the greatest possible speed, which reduces to a minimum any pain felt by the patient during the puncturing procedure.

From the view according to FIG. 3a, it will be seen that the continuous band 84 (compare also the view according to FIG. 7) in which the individual lancets 26 are individually spaced apart from one another is enclosed by the sterile protective band of film acting as film pouch 50 and is connected to the band of film 88 via the underside 82 of the film pouch 50, by means of an adhesive layer 86. The adhesive layer 86 can be a two-sided adhesive band or a hot-melt adhesive. After sterilization of the continuous band 84 with the lancets 26 packed in the film pouches 50, the adhesive layer 86 is applied to that side of the support, band 88 of the test elements 14 lying opposite the electrode structure 96. Excess material, both of the sterile protective band of film of the film pouch 50 and also of the support band 88 and spacer layer 90 in which the pilot holes 112 are located (compare view according to FIGS. 4 and 5), is removed. The individual lancet systems 10 can then be packed individually or in groups into cartons, magazines or blister packs.

The spacer layer 90 shown in FIG. 5 comprises parts of the capillary channels 92, which are punched into the latter. When an edge area of the spacer layer 90 is detached along a detachment edge 110, openings of the capillary channels 92 are obtained which lie at the front edge 16 (compare view according to FIG. 2) of the finished lancet system 10. The support film 88 shown schematically in FIG. 5, with the affixed spacer layer 90, additionally comprises pilot holes 112 which are arranged along opposite edges 108 and are spaced apart from one another by a distance corresponding to an integral multiple of the width of the test elements 14. The pilot holes 112 permit an exact orientation of the individual layers 88, 90 and 72 and of the band 84 and of the sterile protective band of film relative to one another.

Figure 6:
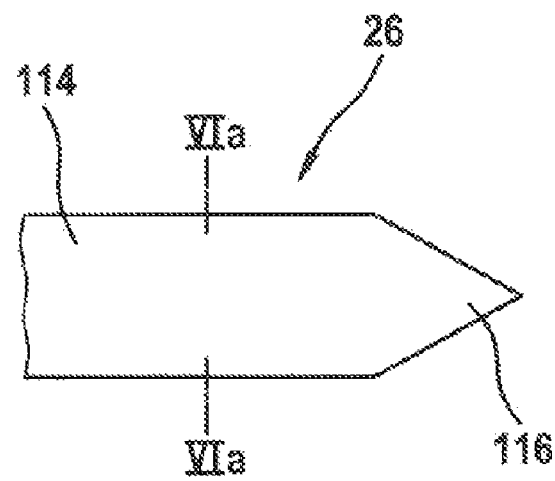
FIG. 6 shows an alternative embodiment of the lancet.
Figure 6A:
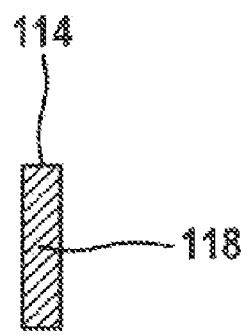
FIG. 6a shows a cross section through the alternative embodiment of the lancet according to FIG. 6.

The views according to FIGS. 6 and 6a show an alternative embodiment variant of the lancet 26 shown in FIG. 1. Instead of the lancet 26 shown in FIG. 1 having a circular cross section and being designed as a needle, the lancet 26 can also be made as a flat lancet 114 from steel. The cross section of the flat lancet 114 shown in FIG. 6 can be rectangular, for example, as is indicated by reference number 118 in FIG. 6a. It is equally possible for the lancet 26 to be designed with a square cross section, although this is not shown in the drawing, since it is simply a geometric variation of the embodiment of the lancet 26 according to FIGS. 6 and 6a.

In a manner analogous to the way in which the lancet 26 designed as a needle is mounted elastically in the illustrative embodiment of the lancet system 10 shown in FIG. 1, the flat lancet 114 shown in FIGS. 6 and 6a can likewise be enclosed by a plastic sheath 34 and can be connected by at least two cords 38 of the elastomer spring 36 to the first and second widened areas 42 and 44 serving as spring abutments 40 on the peripheral edge 56 of the test element 14. Depending on the angle position of the at least two individual cords 38 of the elastomer spring 36, which extend on both sides of the lancet 26 mounted centrally on the test element 14, and depending on the spring characteristics of the material from which the continuous band 84 is made, the speed of the return movement and the puncturing speed to be applied by the puncturing drive mechanism can be configured so that the puncturing procedure for withdrawal of a body fluid can be carried out in a way that causes the patient the least possible pain.

The view according to FIG. 7 shows a continuous band containing a plurality of lancets spaced apart from one another.

It will be seen from the view according to FIG. 7 that the individual lancets 26 of the lancet system 10 are each elastically mounted between widened areas 42, 44 via cords, threads or strips 38. Lying at the end remote from the lancet tip 28 of each individual lancet 26 is the blunt end face 30 of the lancet 26, on which end face 30 a ram provided in the appliance acts in order to move the lancet 26 forwards. The continuous band 84 shown in a plan view in FIG. 7 and containing individual lancets 26 is shown in the cross-sectional view of the lancet system 10 according to FIG. 3.

It is noted that terms like "preferably", "commonly", and "typically" are not utilized herein to limit the scope of the claimed invention or to imply that certain features are critical, essential or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation, The term "substantially" is also utilized herein to represent the degree by which a quantitative representation may vary from a stated reference without resulting in a change in the basic function of the subjects matter at issue.

Having described the invention in detail and by reference to specific embodiments thereof, it well be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An analytical system for detecting an analyte in a body fluid, the system comprising:
    a test strip; and
    a lancet movable relative to the test strip and received on the test strip, wherein a lancet body of the lancet is connected elastically and directly to the test strip via an elastomer spring, wherein the elastomer spring comprises at least two cords of elastomer material and wherein one end of one of the at least two cords is secured centrally on the lancet body and the other end of the one of the at least two cords is affixed on one of two longitudinal sides of the test strip and one end of the other of the at least two cords is secured centrally on the lancet body and the other end of the other of the at least two cords is affixed on the other of two longitudinal sides of the test strip.

2. The system according to claim 1, wherein the lancet is oriented parallel to a longitudinal axis of the test strip.

3. The system according to claim 1, wherein the elastomer spring has a resilient area that extends on both sides of the lancet.

4. The system according to claim 3, wherein the resilient area is designed in the form of a cord, or a thread or a strip.

5. The system according to claim 3, wherein the resilient area of the elastomer spring is defined by incisions, punches or cuttings made in the elastomer material.

6. The system according to claim 3, wherein the elastomer spring is made of a rubber elastic material.

7. The system according to claim 3, wherein the elastomer spring, in the resilient area, has a reduced thickness of less than 200 µm.

8. The system according to claim 3, wherein the resilient area extends from the lancet body of the lancet to a first longitudinal side and to a second longitudinal side of the test strip.

9. The system according to claim 8, wherein on the first longitudinal side and on the second longitudinal side of the test strip, there are first and second widened areas, respectively, which serve as spring abutments of the elastomer spring.

10. The system according to claim 9, wherein the first and second widened areas are designed in a thickness which corresponds to ¼ to ⅝ of the thickness of the lancet.

11. The system according to claim 9, wherein the first and second widened areas of the test strip, on the first and second longitudinal sides of the test element, are offset, with respect to the longitudinal axis of the test strip, in relation to a plastic sheath of the lancet.

12. The system according to claim 1, wherein the lancet has a lancet tip that is flush with a capillary which extends on a front face or on a rear face of the test strip and which opens out on a front edge of the lancet system.

13. The system according to claim 1, wherein the lancet is sealed in a sterile manner by a film pouch made from a sterile protective band of film.

14. The system according to claim 13, wherein the film pouch is connected to the test strip along a peripheral edge thereof.

15. The system according to claim 13, wherein the film pouch is provided, on a front edge of the lancet system, with a fold.

16. The system according to claim 1, wherein a recess contour is created in a surface of the test strip, inside the recess a blunt end of the lancet can be exposed.

17. The system according to claim 1, wherein the lancet is designed in the form of a needle with a circular cross section or is designed as a flat lancet which has a substantially rectangular cross section.

18. The system according to claim 1, wherein the length of the lancet is shorter than the longitudinal extent of the test strip to which the lancet is elastically connected.

19. An analytical system for detecting an analyte in a body fluid, the system comprising:
    a test strip; and
    a lancet movable relative to the test strip and received on the test strip, wherein a lancet body of the lancet is connected elastically and directly to the test strip via an elastomer spring, wherein the elastomer spring comprises a cord of elastomer material of which the cord's ends are secured to opposite longitudinal sides of the test strip and wherein the lancet body is secured centrally on the elastomer spring.

* * * * *